United States Patent [19]

Luckenbaugh

[11] 4,368,068
[45] Jan. 11, 1983

[54] BENZOTRIAZINE DERIVATIVES AS SELECTIVE WEED CONTROL AGENTS

[75] Inventor: Raymond W. Luckenbaugh, Wilmington, Del.

[73] Assignee: E. I. Du Pont de Nemours and Company, Wilmington, Del.

[21] Appl. No.: 225,188

[22] Filed: Jan. 15, 1981

[51] Int. Cl.³ .................. C07D 253/08; C07D 401/12; A01N 43/64; C07D 413/12
[52] U.S. Cl. ........................................ 71/93; 544/183; 542/416; 542/427
[58] Field of Search ................ 544/183; 542/416, 439, 542/427; 71/92, 93

[56] References Cited

U.S. PATENT DOCUMENTS 4,309,211  1/1982  Serban et al. ...................... 544/183

Primary Examiner—John M. Ford

[57] ABSTRACT

This invention relates to herbicidal benzotriazine derivatives, herbicidal compositions containing said derivatives, and methods of using said derivatives as herbicides.

15 Claims, No Drawings

BENZOTRIAZINE DERIVATIVES AS SELECTIVE WEED CONTROL AGENTS

BACKGROUND OF THE INVENTION

This invention relates to benzotriazine derivatives which are useful as selective weed control agents. The compounds are especially useful for controlling grass weeds in broadleaf crops such as soybeans.

The presence of undesirable vegetation causes substantial damage to useful crops, especially agricultural products that satisfy man's basic food and fiber needs, such as cotton, soybeans, beans and the like. The current population explosion and concomitant world food and fiber shortage underlie the need for improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

This invention relates to novel compounds of Formula I, to their agricultural compositions, and to their method of use as pre- and post-emergence herbicides.

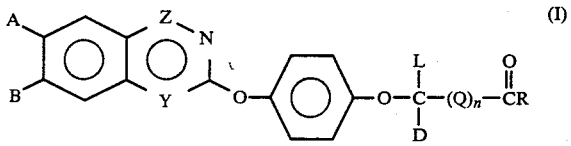

wherein
A is H, Cl, Br, F, $CF_3$, $CH_3$ or $CH_3O$;
B is H or Cl;
D is H, $CH_3$ or $CO_2R_8$;
L is H or $CH_3$;
Q is $-CH=CH-$ or $-CH_2CH_2-$;
n is 0 or 1;
R is Cl, $XR_1$, $NR_2R_3$, OH or OM;
M is an agriculturally suitable salt;
$R_1$ is $C_1-C_4$ alkyl, benzyl, phenyl, $C_5-C_8$ cycloalkyl, $-CH_2CH_2OCH_3$, $-CH_2CH_2OCH_2CH_3$, $CH_2CH_2CH_2OCH_3$, $C_3-C_4$ alkenyl, $C_3-C_4$ alkynyl, $-N=CR_6R_7$ or $C_3-C_4$ alkenyl or alkynyl optionally substituted with one Cl;
$R_2$ is H, $C_1-C_4$ alkyl, $C_5-C_8$ cycloalkyl, benzyl, phenyl, $-OCH_3$, $C_3-C_4$ alkenyl or $-CH_2CH_2NR_4R_5$;
$R_3$ is H or $C_1-C_4$ alkyl; or
$R_2$ and $R_3$ may be taken together to be $-(CH_2)_2-O-(CH_2)_2-$, $-(CH_2)_4-$, $-(CH_2)_5-$, $-(CH_2)_6-$ or $-(CH_2)_2-N-(CH_3)(CH_2)_2-$;
$R_4$ and $R_5$ are independently methyl or ethyl;
$R_6$ is H or $C_1-C_4$ alkyl;
$R_7$ is H or $C_1-C_4$ alkyl; or
$R_6$ and $R_7$ may be taken together to be $-(CH_2)_5-$ or $-(CH_2)_4-$;
$R_8$ is $C_1-C_4$ alkyl;
X is 0 or S; and
Y and Z are independently N or $N\rightarrow O$;
provided that:

(a) when D is $CO_2R_8$, then n is 0 and L is $CH_3$;
(b) when $R_1$ is $-N=CR_6R_7$, then X is 0;
(c) $R_2$ and $R_3$ together contain no more than 8 carbon atoms;
(d) one of $R_6$ and $R_7$ is other than H;
(e) when A is other than Cl, then B is H;
(f) when B is Cl, then L is H, D is $CH_3$, n is 0, R is $XR_1$, and X is 0.

Preferred in order of increasing activity and/or increasingly favorable ease of synthesis are those compounds of Formula I wherein:
(1) D is $CH_3$ and L is H;
(2) compounds of preferred (1) wherein Y is N;
(3) compounds of preferred (2) wherein $R_1$ is $C_1-C_4$ alkyl;
(4) compounds of preferred (3) wherein n is 0.

Specifically preferred for its excellent activity and/or most favorable ease of synthesis is: Methyl 2-[4-[(7-chloro-1-oxide-1,2,4-benzotriazin-3-yl)oxy]phenoxy]-propanoate.

SYNTHESIS

The compounds of Formula I can be prepared in a number of ways, depending on the definitions of D, Q, n and R.

(a.) Compounds of Formula I where D=H or $CH_3$, n=0, $Z=N\rightarrow O$ and Y=N.

(i) Several routes are available for preparing these compounds. Compounds where $R=XR_1$, X=0 and $R_1=C_1-C_4$ alkyl, represented by Formula IIa, can be prepared by combining, preferably in equimolar amounts, a 3-chlorobenzotriazine-1-oxide and the alkali metal salt of the alkyl 2-(4-hydroxyphenoxy)alkanoate as illustrated in Reaction 1.

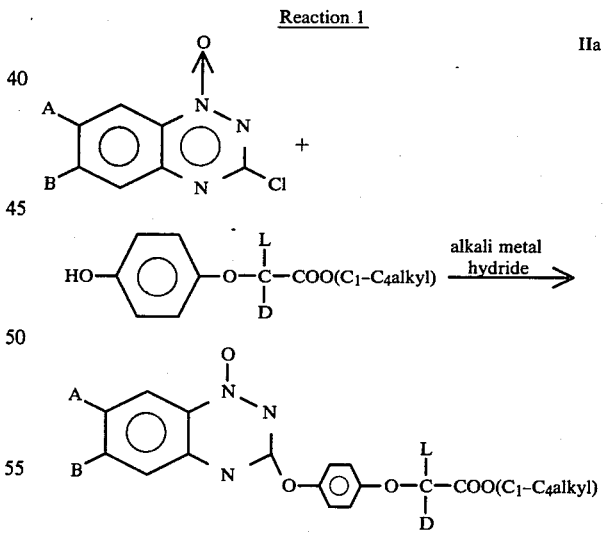

where A, B and L are as previously defined and D=H or $CH_3$.

Suitable solvents for this reaction include dimethylformamide, dimethylsulfoxide, diglyme and methylethylketone. The reaction is preferably carried out at a temperature between about 25° and about 130° C. The esters of Formula IIa are useful starting materials for preparing other compounds of this invention.

The 3-chlorobenzotriazine-1-oxides used in this reaction can be prepared by methods known in the art.

Cyanamide is condensed with an o-nitroaniline to yield an o-nitrophenylguanidine which is cyclized in 30% KOH to the 3-aminobenzotriazine-1-oxide as described in *J. Am. Chem. Soc.*, 76, 3551 (1954). The 3-aminobenzotriazine-1-oxide is converted to the 3-hydroxybenzotriazine-1-oxide by diazotization as described in *J. Org. Chem.*, 24, 813 (1959). The 3-hydroxybenzotriazine-1-oxide is treated with thionyl chloride and DMF or POCl$_3$ as described in U.S. Pat. No. 4,206,212 or *J. Org. Chem.*, 24, 813 (1959) to give the desired 3-chlorobenzotriazine-1-oxides. Alternatively, they may be synthesized by treatment of an o-nitroaniline with phosgene and then ammonia to give the urea as described in U.S. Pat. No. 4,206,212. The urea is cyclized as before in base and the resulting 3-hydroxybenzotriazine-1-oxide converted to the 3-chloro derivative by the previously disclosed methods. The disclosures of the above-cited references are hereby incorporated by reference.

The alkyl 2-(4-hydroxyphenoxy)alkanoates used in the reaction are known in the art and can be prepared in a two-step process from commercially available compounds. First, 4-benzyloxyphenol is alkylated by reaction with an alkyl bromoalkanoate. The product is hydrogenated in the presence of a palladium over carbon catalyst to yield the desired compound.

(ii) Compounds where R=OH, represented by Formula IIb, can be prepared by hydrolysis of an ester of Formula IIa.

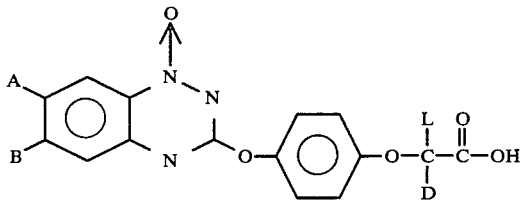
IIb where A, B and L are as previously defined and D=H or CH$_3$.

Either acid hydrolysis with, for example, dilute hydrochloric or sulfuric acid, or basic hydrolysis with, for example, sodium hydroxide or potassium hydroxide, followed by acidification with dilute acid yields the acids of Formula IIb.

(iii) The acids of Formula IIb may be treated with excess thionyl chloride to yield the acid chlorides of Formula IIc, where R=Cl.

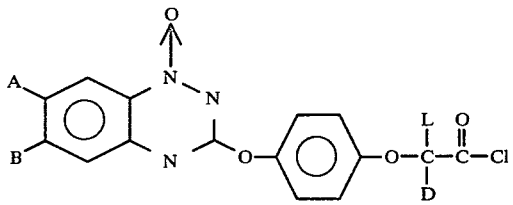
IIc where A, B and L are as previously defined and D=H or CH$_3$.

(iv) Compounds where R=NR$_2$R$_3$, represented by Formula IId, can be prepared by combining an acid chloride of Formula IIc with two moles of the appropriate amine:

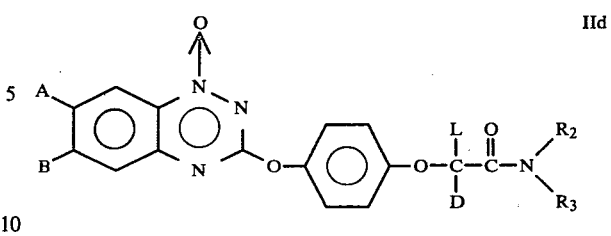
IId where A, B and L are as previously defined and D=H or CH$_3$.

The acid chloride and amine are preferably combined at or below ambient temperature in a solvent such as tetrahydrofuran or methylene chloride.

(v) Compounds where R=XR$_1$, represented by Formula IIe, are prepared by combining an acid chloride of Formula IIc with the appropriate alcohol, thiol, phenol, thiophenol or oxime in the presence of an equimolar amount of an acid acceptor:

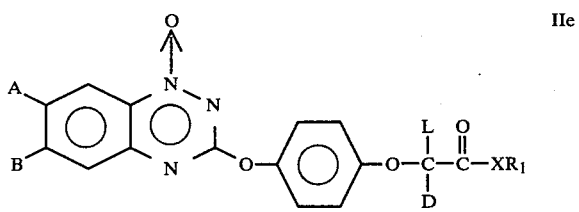
IIe where A, B, L, X and R$_1$ are as previously defined and D=H or CH$_3$.

Suitable acid acceptors include pyridine and N,N-dimethylaniline. The reaction is preferably run under a nitrogen atmosphere at a temperature of from about 0° to about 40° C.

(vi) Agriculturally suitable salts of the acids of Formula IIb are useful herbicides and include, but are not limited to, ammonium, sodium, lithium, potassium, calcium, magnesium, barium and quaternary ammonium salts. These salts can be represented by the general formula IIf where Z=N→O, Y=N, D=H or CH$_3$ and n=0 and can be prepared by a number of known methods.

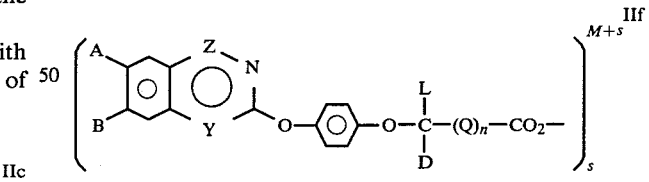
IIf where A, B, Z, Y, L, D, Q, n and M are as previously defined and s is 1 or 2.

For example, metal salts can be prepared by treating compounds of Formula IIb with a solution of an alkali or alkaline earth metal salt having a sufficiently basic anion (e.g., hydroxide, alkoxide, carbonate or hydride). Ammonium, amine and quaternary ammonium salts can be made by similar techniques.

(b) Compounds of Formula I where D=H or CH$_3$; Q=—CH=CH—, n=1, Z=N→O and Y=N.

These compounds, represented by Formula III, are also prepared according to different methods, depending on the definition of R.

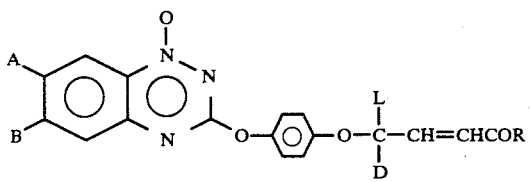

where A, B, L and R are as previously defined and D=H or CH₃.

Compounds of Formula III where R=XR₁, X=O and R₁=C₁-C₄ alkyl are prepared as illustrated in Reaction 2.

Reaction 2

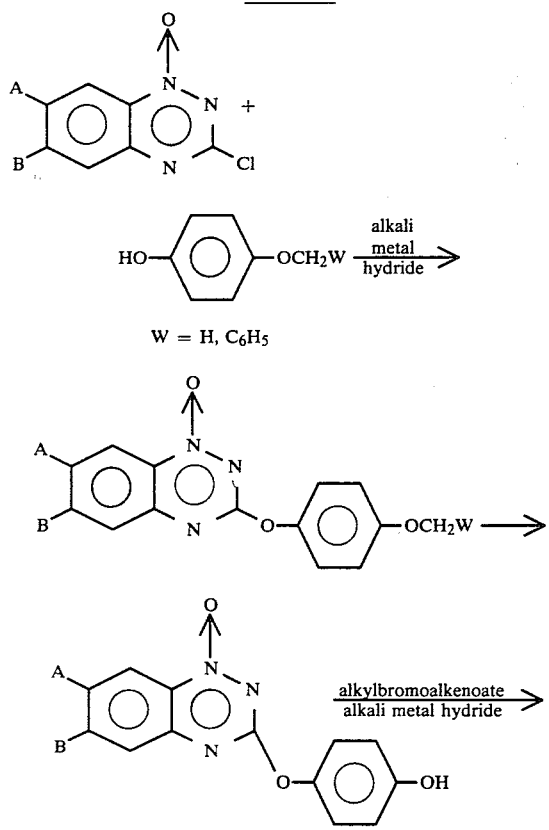

where R=XR₁, X=O and R₁=C₁-C₄ alkyl.

A 3-chlorobenzotriazine-1-oxide is condensed with 4-benzyloxyphenol or 4-methoxyphenol in the presence of sodium methoxide or an alkali metal hydride. Next, the methyl or benzyl group is removed by methods known in the art, for example those described in Belgian Pat. No. 868,875 or *Tetrahedron*, 24, 2289 (1968), both herein incorporated by reference, to yield a 3-(4-hydroxyphenoxy)-1,2,4-benzotriazine-1-oxide. Interaction of this product with an alkyl bromoalkenoate in the presence of an alkali metal hydride or carbonate yields the desired esters.

The esters of Formula III may be used to prepare the acids, acid chlorides, amides and other esters of this invention as well as the salts of these compounds, by methods identical to those used to prepare the corresponding compounds of Formulas IIb-IIf.

(c) Compounds of Formula I where D=CO₂R₈, L=CH₃, n=0, Z=N→O and Y=N.

There are two basic routes available for preparing these compounds, represented by Formula IV.

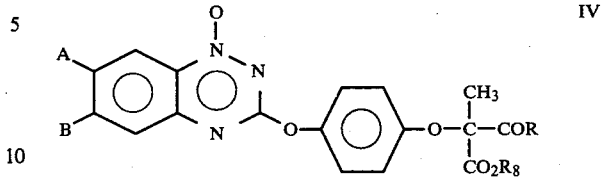

where A, B, R and R₈ are as previously defined.

Compounds of Formula IV where R=NR₂R₃ or C₁-C₄ alkoxy can be prepared by combining a substituted 3-chlorobenzotriazine-1-oxide and the alkali metal salt of the appropriate phenol, preferably at a temperature between about 25° and 130° C. Suitable solvents include DMF. The phenols can be prepared by procedures similar to those outlined previously in relation to the preparation of alkyl 2-(4-hydroxyphenoxy)propanoates.

Alternatively, the compounds of Formula IV where R=NR₂R₃ or C₁-C₄ alkoxy can be prepared by contacting the appropriate 3-(4-hydroxyphenoxy)benzotriazine-1-oxide with a halogenated malonic acid derivative, Hal-C(CH₃)(CO₂R₈)(COR).

The resulting compounds, when R=C₁-C₄ alkoxy, can be used as starting materials for preparing the acids, acid chlorides and other esters of this invention as well as the salts of these compounds by methods similar to those used to prepare the corresponding compounds of Formulas IIb, IIc, IIe and IIf.

(d) Compounds of Formula I where D=H or CH₃, Q=—CH₂CH₂, n=1, Z=N→O and Y=N.

The compounds represented by Formula V are prepared as follows:

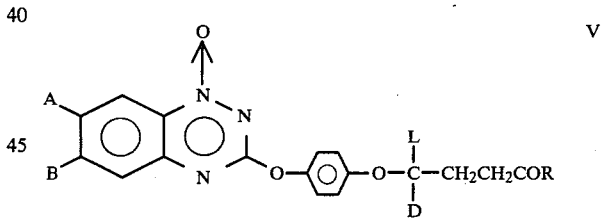

where A, B, L, D and R are as previously defined.

To prepare a compound of Formula V where R=C₁-C₄ alkoxy, the appropriate 3-chloro-1,2,4-benzotriazine-1-oxide is contacted, preferably in equimolar amounts, with the appropriate alkyl 4-(4-hydroxyphenoxy)alkanoate in the presence of potassium carbonate. Suitable solvents include acetonitrile, dimethylformamide or methylethylketone. This sequence is illustrated in Reaction 3:

Reaction 3

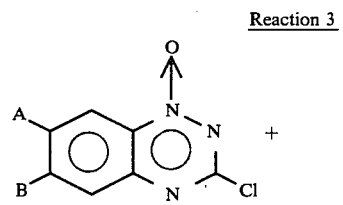

-continued
Reaction 3

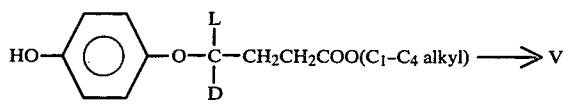

The alkyl 4-(4-hydroxyphenoxy)alkanoates can be prepared by alkylation of the commercially available 4-benzyloxyphenol with the alkylbromoalkenoate, followed by catalytic hydrogenation to reduce the unsaturation and remove the benzyl group.

The compounds thus prepared are used as starting materials to prepare the acids, acid chlorides, amides, salts and other esters of this invention by methods similar to those used for preparing the corresponding compounds of Formulas IIb–IIf.

(e) Compounds of Formula I where Z and Y=N→O and R≠SR$_1$, O-alkenyl, O-alkynyl, N-alkenyl or

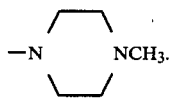

These compounds represented by Formula VI, can be prepared by combining the appropriate benzotriazine-1-oxide with a peracid, such as perbenzoic acid, in a suitable solvent, such as methylene chloride.

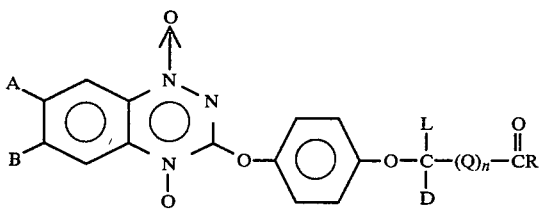

where A, B, D, L, Q, n and R are as previously defined.

Compounds of Formula VI where R=SR$_1$, O-alkenyl, O-alkynyl, N-alkenyl, or

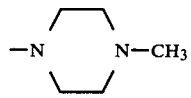

may be prepared from the appropriate compound VI where R=Cl and the thiol or thiophenyl, alcohol or amine in the presence of an acid acceptor.

(f) Compounds of Formula I where Z and Y=N.

These compounds, represented by Formula VII, can be prepared from the appropriate 3-(4-hydroxyphenoxy)-1,2,4-benzotriazine or the 3-chloro-1,2,4-benzotriazine by methods that are clearly described elsewhere in this application. In addition, some of the compounds can be prepared by reduction of the corresponding N→O compounds by literature methods such as catalytic hydrogenation or zinc acetic acid reduction.

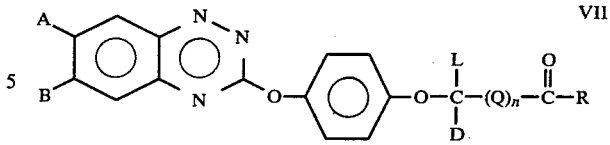

where A, B, D, L, Q, n and R are as previously defined.

(g) Compounds of Formula I where Z=N, Y=N→O, and R≠SR, O-alkenyl, O-alkynyl, N-alkenyl or

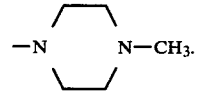

These compounds, represented by Formula VIII, can be prepared by oxidation of 1,2,4-benzotriazines with a peracid such as perbenzoic or peracetic acid.

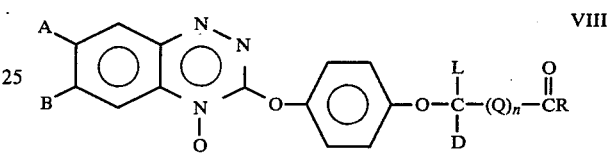

where A, B, D, L, Q, n and R are previously defined.

Compounds of type VIII where R=SR$_1$, O-alkenyl, O-alkenyl or

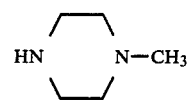

can be prepared as outlined under (e).

The following examples illustrate the preparation of some of the compounds of the invention.

EXAMPLE 1

Methyl 2-[4-[(7-chloro-1-oxide-1,2,4-benzotriazin-3-yl)-oxy]-phenoxy]propanoate

In a nitrogen atmosphere, a solution of 0.97 g (4.9 mmoles) methyl 2-(4-hydroxyphenoxy)propanoate in 2 cc of dimethylformamide was added dropwise at about 15° C. to 0.24 g (5 mmoles) 50% sodium hydride in 10 cc dimethylformamide. The reaction was allowed to warm to room temperature after the addition was complete. When the evolution of hydrogen ceased, 1.06 g (4.9 mmoles) 3,7-dichloro-1,2,4-benzotriazine-1-oxide was added and the reaction mixture was warmed at 80° C. for 1 hour. The reaction mixture was poured into crushed ice and water. The precipitated solid was extracted with ether, and the extracts were washed twice with water, dried and concentrated. Residual oil from the NaH used was removed by taking up the product in MeOH and washing with hexane. Evaporation of the MeOH gives 0.8 g of the product.

NMR (CDCl$_3$)δ: 1.7 (d, 3H); 3.8 (s, 3H); 4.8 (q, 1H); 7.0 (ABq, 4H); 7.8 (m, 3H).

Following the teachings of Example 1 and by substituting an appropriate 3-chloro-1,2,4-benzotriazine-1-oxide and an appropriate alkyl 2-(4-hydroxyphenoxy)- propanoate, the compounds listed in Table I can be prepared.

TABLE I

[Structure: benzotriazine N-oxide with A, B substituents on benzene ring, connected via O-phenyl-O-C(L)(D)-C(=O)-XR₁]

| A | B | X | R₁ | L | D | m.p.(°C.) |
|---|---|---|---|---|---|---|
| Cl | H | O | CH₃ | H | H | 157–161° |
| CH₃ | H | O | CH₃ | CH₃ | CH₃ | |
| H | H | O | CH₃ | CH₃ | CH₃ | |
| F | H | O | CH₃ | H | H | |
| Br | H | O | CH₃ | CH₃ | H | 100–110° |
| OCH₃ | H | O | CH₃ | CH₃ | H | 96–104° |
| Cl | H | O | CH₃ | CH₃ | CH₃ | |
| CF₃ | H | O | CH₃ | CH₃ | H | glass |
| F | H | O | n-C₃H₇ | CH₃ | H | |
| Cl | H | O | n-C₄H₉ | CH₃ | H | |
| Cl | Cl | O | CH₃ | CH₃ | H | glass |
| Cl | H | O | C₂H₅ | CH₃ | H | |
| Cl | H | O | i-C₃H₇ | CH₃ | H | |
| F | H | O | t-C₄H₉ | CH₃ | H | |
| Cl | Cl | O | C₂H₅ | H | CH₃ | |
| Cl | Cl | O | n-C₄H₉ | H | CH₃ | |
| CH₃ | H | O | CH₃ | CH₃ | H | 98–103° |
| H | H | O | CH₃ | CH₃ | H | 131–137° |
| F | H | O | CH₃ | CH₃ | H | 135–145° |
| Cl | H | O | CH₃ | CH₃ | H | glass |

EXAMPLE 2

2-[4-[(7-chloro-1-oxide-1,2,4-benzotriazin-3-yl)-oxy]-phenoxy]propanoic acid 0.01 mole Methyl-2-[4-[(7-chloro-1-oxide-1,2,4-benzotriazin-3-yl)oxy]phenoxy]propanoate is added to a solution of 0.01 mole potassium hydroxide in 5 cc water and 60 cc methanol. The mixture is stirred at room temperature overnight. The methanol is removed under vacuum. Ice and hydrochloric acid are added to the mixture until it is acidic (pH ~2). The precipitated acid is filtered and purified by redissolution into saturated sodium bicarbonate solution, reprecipitation by acidification with dilute hydrochloric acid and crystallization from methanol.

By hydrolysis of the appropriate ester employing procedures similar to that described above, the acids of Formula IIb listed in Table II can be prepared.

TABLE II

[Structure: benzotriazine N-oxide with A, B substituents, connected via O-phenyl-O-C(L)(D)-C(=O)-OH]

| A | B | L | D |
|---|---|---|---|
| Br | H | CH₃ | H |
| F | H | CH₃ | H |
| Cl | H | CH₃ | H |
| OCH₃ | H | CH₃ | H |
| CF₃ | H | CH₃ | H |
| CH₃ | H | CH₃ | H |
| H | H | CH₃ | H |
| Cl | H | CH₃ | CH₃ |
| F | H | H | H |

TABLE II-continued

| A | B | L | D |
|---|---|---|---|
| Cl | Cl | H | CH₃ |

EXAMPLE 3

N,N-Diethyl-2-[4-[(7-chloro-1-oxide-1,2,4-benzotriazin-3-yl)oxy]phenoxy]propanamide The title compound can be prepared as follows. Interaction of 2-[4-[(7-chloro-1-oxide-1,2,4-benzotriazin-3-yl)oxy]phenoxy]propanoic acid with thionyl chloride in a suitable solvent such as chlorobutane gives the acid chloride. A solution of 0.01 mole 2-[4-[(7-chloro-1-oxide-1,2,4-benzotriazin-3-yl)oxy]phenoxy]propionyl chloride in 30 cc methylene chloride is added to a cold (5° C.) solution of 0.025 mole diethylamine in 30 cc methylene chloride. The mixture is stirred at room temperature overnight. The methylene chloride solution is washed with water and dried over magnesium sulfate. The methylene chloride is removed under vacuum to yield N,N-diethyl-2-[4-[(7-chloro-1-oxide-1,2,4-benzotriazin-3-yl)oxy]phenoxy]-propanamide.

By treatment of the appropriate acid chloride with an amine using the procedure of Example 3, the amides of Formula IId listed in Table III can be prepared.

TABLE III

[Structure: benzotriazine N-oxide with A, B substituents, connected via O-phenyl-O-C(L)(D)-C(=O)-N(R₂)(R₃)]

| A | B | R₂ | R₃ | L | D |
|---|---|---|---|---|---|
| CF₃ | H | H | H | CH₃ | H |
| Br | H | H | CH₃ | CH₃ | H |
| F | H | phenyl | H | H | H |
| F | H | C₆H₅ | H | CH₃ | H |
| CF₃ | H | C₆H₅CH₂— | H | CH₃ | H |
| OCH₃ | H | H | (CH₃)₂CH— | CH₃ | H |
| CF₃ | H | t-C₄H₉ | H | CH₃ | H |
| CH₃ | H | CH₃ | CH₃ | CH₃ | H |
| Cl | H | n-C₄H₉ | CH₃ | CH₃ | H |
| CF₃ | H | —(CH₂)₂—O—(CH₂)₂— | | H | H |
| Cl | H | —(CH₂)₄— | | CH₃ | CH₃ |
| OCH₃ | H | —(CH₂)₅— | | CH₃ | H |
| Br | H | —(CH₂)₆— | | CH₃ | H |
| Cl | H | i-C₄H₉ | H | CH₃ | H |
| Cl | H | CH₃O— | CH₃ | CH₃ | H |
| H | H | C₂H₅ | H | CH₃ | H |
| CF₃ | H | H | (CH₂)₃CH₃ | CH₃ | H |
| Cl | H | —(CH₂)₂—N(CH₃)—(CH₂)₂— | | CH₃ | H |
| Cl | Cl | CH₂—CH=CH₂ | H | H | CH₃ |
| Br | H | CH₂CH₂N(CH₃)₂ | H | H | H |
| Cl | Cl | CH₃ | CH₃ | H | CH₃ |
| Cl | H | H | CH₂CH₃ | CH₃ | H |
| Cl | H | CH₂CH₂CH₃ | H | H | CH₃ |

TABLE III-continued

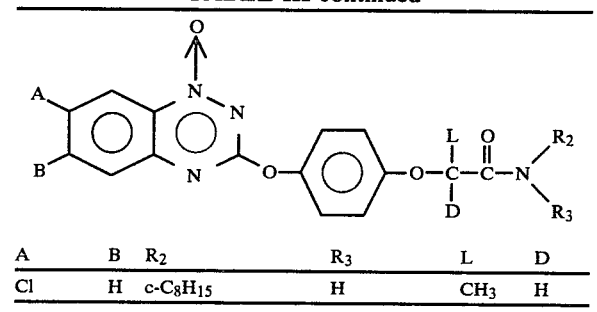

| A | B | R₂ | R₃ | L | D |
|---|---|---|---|---|---|
| Cl | H | c-C₈H₁₅ | H | CH₃ | H |

EXAMPLE 4

Allyl-2-[4-[(7-chloro-1-oxide-1,2,4-benzotriazin-3-yl)oxy]phenoxy]propanoate

The following procedure can be employed to make the title compound.

To a solution of 1.2 g allyl alcohol and 1.6 g pyridine in 50 cc methylene chloride, add 6.6 g of 2-[4-[(7-chloro-1-oxide-1,2,4-benzotriazin-3-yl)oxy]phenoxy]-propionyl chloride in 60 cc methylene chloride. Stir the mixture at room temperature overnight. Wash the methylene chloride solution with water, dry the solution over magnesium sulfate and concentrate under vacuum to give allyl 2-[4-[(7-chloro-1-oxide-1,2,4-benzotriazin-3-yl)oxy]phenoxy]propanoate.

By treatment of the appropriate acid chloride with the appropriate alcohol, thiol, phenol, thiophenol or oxime as described above, the compounds of Formula IIe listed in Table IV can be obtained.

TABLE IV

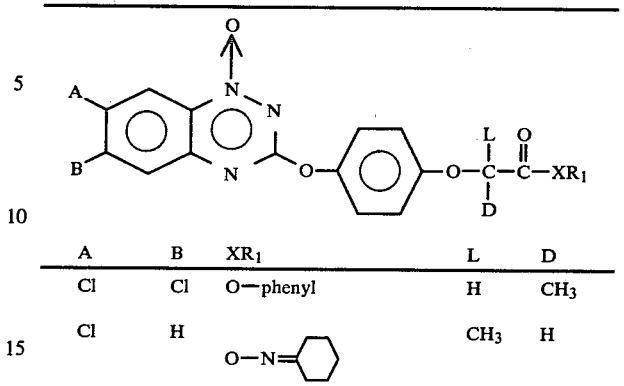

| A | B | XR₁ | L | D |
|---|---|---|---|---|
| CF₃ | H | O—phenyl | CH₃ | H |
| Br | H | OCH₂CH₂OCH₃ | CH₃ | H |
| Cl | H | OCH₂—C≡C—CH₂Cl | CH₃ | H |
| F | H | OC₆H₅ | CH₃ | H |
| Br | H | OCH₂C₆H₅ | H | H |
| OCH₃ | H | OCH₂CH₂OC₂H₅ | CH₃ | H |
| CF₃ | H | OCH₂CH₂CH₂OCH₃ | CH₃ | CH₃ |
| CH₃ | H | O—phenyl | CH₃ | H |
| Cl | H | SCH₃ | H | H |
| OCH₃ | H | SC₆H₅ | CH₃ | H |
| Br | H | SCH₂CH=CH₂ | CH₃ | H |
| F | H | SCH₂C₆H₅ | CH₃ | CH₃ |
| H | H | S—phenyl | CH₃ | H |
| Cl | H | SC₂H₅ | CH₃ | H |
| F | H | SC₃H₇ | CH₃ | CH₃ |
| Cl | H | SC₄H₉ | CH₃ | H |
| Cl | H | OCH₂—C≡C—CH₂Cl | CH₃ | H |
| Cl | Cl | OCH₂—C≡C—CH₂Cl | H | CH₃ |
| Cl | H | O—N=C(CH₃)₂ | CH₃ | CH₃ |
| Cl | H | O—N=⬠ | CH₃ | H |
| F | H | O—N=CH(C₄H₉) | H | H |
| Cl | Cl | O—N=C(CH₃)(C₂H₅) | H | CH₃ |
| Cl | Cl | OCH₃ | H | CH₃ |
| Cl | Cl | OC₄H₉ | H | CH₃ |
| Cl | Cl | O—cyclohexyl | H | CH₃ |

TABLE IV-continued

| A | B | XR₁ | L | D |
|---|---|---|---|---|
| Cl | Cl | O—phenyl | H | CH₃ |
| Cl | H | O—N=⬡ | CH₃ | H |

EXAMPLE 5

Sodium 2-[4-[(7-chloro-1-oxide, 1,2,4-benzotriazin-3-yl)oxy]phenoxy]propanoate

The following method can be employed to synthesize the sodium salt.

Add 0.01 mole 2-[4-[(7-chloro-1-oxide-1,2,4-benzotriazin-3-yl)oxy]phenoxy]propionic acid to a solution of 0.01 mole sodium methoxide in 50 cc methanol. Stir the mixture at room temperature for 2 hours and remove the solvent under vacuum to yield the title compound.

By treatment of the appropriate carboxylic acid with a suitable base (for example, ammonia, an amine, a quaternary ammonium hydroxide, an alkali metal or an alkaline earth hydroxide, hydride, carbonate or bicarbonate) the carboxylic acid salts listed in Table V may be prepared.

TABLE V

| A | B | S | M | L | D |
|---|---|---|---|---|---|
| H | H | 1 | Na | CH₃ | H |
| CF₃ | H | 1 | Na | CH₃ | CH₃ |
| Br | H | 1 | Na | CH₃ | H |
| F | H | 1 | Na | CH₃ | H |
| Cl | Cl | 1 | K | H | CH₃ |
| Br | H | 1 | K | CH₃ | H |
| OCH₃ | H | 1 | Li | CH₃ | H |
| CF₃ | H | 1 | Li | CH₃ | CH₃ |
| CH₃ | H | 1 | NH₄ | CH₃ | H |
| Cl | H | 1 | NH₄ | H | H |
| CF₃ | H | 1 | CH₃NH₃ | H | H |
| Cl | H | 1 | (HOCH₂CH₂)₂NH₂ | CH₃ | H |
| OCH₃ | H | 1 | (CH₃)₂NH₂ | H | H |
| Br | H | 1 | (C₂H₅)₃NH | CH₃ | CH₃ |
| F | H | 1 | (HOCH₂CH₂)₃NH | CH₃ | H |
| Cl | H | 1 | (HOCH₂CH₂)₃NH | CH₃ | H |
| Cl | H | 1 | C₄H₉NH₃ | CH₃ | H |
| F | H | 2 | Ca | CH₃ | H |
| Cl | H | 2 | Ca | CH₃ | H |
| Cl | H | 2 | Mg | CH₃ | H |
| CF₃ | H | 2 | Mg | CH₃ | H |

EXAMPLE 6

3-(4-Benzyloxyphenoxy)-7-chloro-1,2,4-benzotriazine-1-oxide

In a nitrogen atmosphere, a solution of 0.1 mole 4-benzyloxyphenol in 50 cc dimethylformamide is added dropwise at about 15° C. to 0.1 mole 57% sodium hydride in 25 cc dimethylformamide. When evolution of hydrogen ceases, 0.1 mole 3,7-dichloro-1,2,4-benzotriazine-1-oxide is added and the reaction mixture is heated at 125° C. for about 2 hours. After standing overnight at room temperature, the reaction mixture is poured into ice-water (~500 cc). The solid product is filtered and crystallized from methanol or acetonitrile.

Following the procedure of Example 6 and by condensing the appropriate 3-chlorobenzotriazine with 4-benzoyloxyphenol or 4-methoxyphenol, other useful 3-(4-benzyloxyphenoxy)-1,2,4-benzotriazine-1-oxide intermediates can be prepared.

EXAMPLE 7

3-(4-Hydroxyphenoxy)-7-chloro-1,2,4-benzotriazine-1-oxide

A solution of 0.05 mole borontribromide in 100 cc methylene chloride is added, dropwise, to a well stirred cold (−62°) solution of 3-(4-benzyloxyphenoxy)-1,2,4-benzotriazine-1-oxide (0.05 mole) in 400 cc methylene chloride. When the addition is complete, the temperature of the reaction is allowed to rise slowly to room temperature. The reaction mixture is then poured into 1 liter of water and an additional 500 cc of methylene chloride is added. The mixture is stirred vigorously for 40 minutes and the insoluble solid is filtered.

Other 3-(4-hydroxyphenoxy)-1,2,4-benzotriazine-1-oxide intermediates can be prepared from the appropriate ether by the procedure described above.

EXAMPLE 8

Methyl 4-[4-[(7-chloro-1-oxide-1,2,4-benzotriazin-3-yl)oxy]phenoxy]pent-2-enoate The following procedure can be used to prepare the title compound.

In a nitrogen atmosphere, add a solution of 0.02 mole 3-(4-hydroxyphenoxy)-7-chloro-1,2,4-benzotriazine-1-oxide in 30 cc dimethylformamide to 0.02 mole 57% sodium hydride in 20 cc dimethylformamide at about 20° C. When the evolution of hydrogen ceases, add 0.02 mole methyl 4-bromo-2-pentenoate. Heat the reaction mixture at approximately 80° C. until the reaction is complete. Pour the reaction mixture into water and extract with ether. Combine the ethereal extracts and dry over magnesium sulfate. Removal of the ether gives the desired product.

The compounds of Formula III listed in the following table can be prepared in a similar fashion from the appropriate 3-(4-hydroxyphenoxy)benzotriazine and an alkyl 4-bromo-2-pentenoate.

TABLE VI

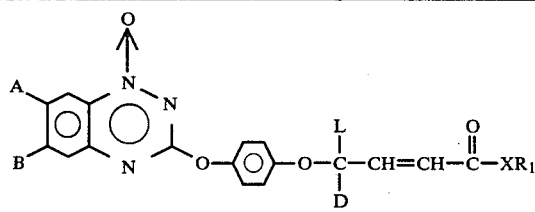

| A | B | XR$_1$ | L | D |
|---|---|---|---|---|
| CF$_3$ | H | OCH$_3$ | H | H |
| Br | H | OCH$_3$ | CH$_3$ | H |
| F | H | OCH$_3$ | CH$_3$ | CH$_3$ |
| OCH$_3$ | H | OCH$_3$ | CH$_3$ | H |
| CH$_3$ | H | OCH$_3$ | CH$_3$ | H |
| Cl | H | O—n-C$_3$H$_7$ | H | H |
| Cl | H | OC$_2$H$_5$ | CH$_3$ | CH$_3$ |
| Cl | H | O—i-C$_3$H$_7$ | CH$_3$ | H |
| F | H | O—t-C$_4$H$_9$ | CH$_3$ | H |
| Cl | H | OCH$_3$ | CH$_3$ | H |
| Cl | H | OC$_4$H$_9$ | CH$_3$ | H |

EXAMPLE 9

4-[4-[(7-Chloro-1-oxide-1,2,4-benzotriazin-3-yl)oxy]phenoxy]pent-2-enoic acid The procedure described under Example 2 can be used to prepare the desired acid.

By hydrolysis of the appropriate ester, the compounds of Formula III listed in Table VII can be prepared.

TABLE VII

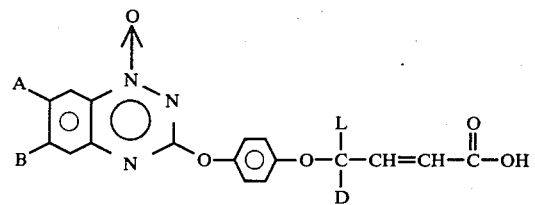

| A | B | L | D |
|---|---|---|---|
| CF$_3$ | H | CH$_3$ | H |
| Br | H | CH$_3$ | H |
| F | H | H | H |
| CH$_3$ | H | CH$_3$ | H |
| Cl | H | CH$_3$ | H |
| Cl | H | CH$_3$ | H |
| Cl | H | CH$_3$ | CH$_3$ |
| F | H | CH$_3$ | H |
| Cl | H | H | H |
| CF$_3$ | H | H | H |
| OCH$_3$ | H | CH$_3$ | H |

EXAMPLE 10

N,N-diethyl-4-[4-[(7-chloro-1-oxide-1,2,4-benzotriazin-3-yl)oxy]phenoxy]pent-2-enamide The method described in Example 3 may be employed to prepare the subject compound. By a similar process, the amides of Formula III listed in Table VIII can be made.

TABLE VIII

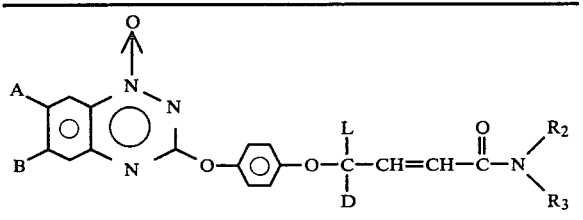

| A | B | R2 | R3 | L | D |
|---|---|---|---|---|---|
| CF3 | H | H | H | CH3 | H |
| Br | H | H | CH3 | CH3 | H |
| F | H | phenyl | H | H | H |
| F | H | C6H5 | H | CH3 | H |
| CF3 | H | C6H5CH2— | H | CH3 | H |
| Cl | H | H | (CH3)2CH— | CH3 | H |
| CF3 | H | t-C4H9 | H | CH3 | H |
| CH3 | H | CH3 | CH3 | CH3 | H |
| Cl | H | n-C4H9 | CH3 | CH3 | H |
| CF3 | H | —(CH2)2—O—(CH2)2— | | H | H |
| Cl | H | —(CH2)4— | | CH3 | CH3 |
| Cl | H | —(CH2)5— | | CH3 | H |
| Br | H | —(CH2)6— | | CH3 | H |
| Cl | H | C4H9 | H | CH3 | H |
| Cl | H | CH3 | CH3O— | CH3 | H |
| H | H | C2H5 | H | CH3 | H |
| CF3 | H | H | phenyl | CH3 | H |
| Cl | H | —(CH2)2—N(CH3)—(CH2)2— | | CH3 | H |
| Cl | H | H | CH2—CH=CH2 | CH3 | CH3 |
| Br | H | H | CH2CH2N(CH3)2 | CH3 | H |
| Cl | H | CH3 | CH3 | H | H |
| OCH3 | H | H | H | CH3 | H |

EXAMPLE 11

Allyl-4-[4-[(7-chloro-1-oxide-1,2,4-benzotriazine-3-yl)oxy]phenoxy]pent-2-enoate The method cited in Example 4 can be utilized to prepare the title compound.

The compounds of Formula III listed in Table IX can be prepared in a similar fashion from the appropriate hydroxy or thio compound.

TABLE IX

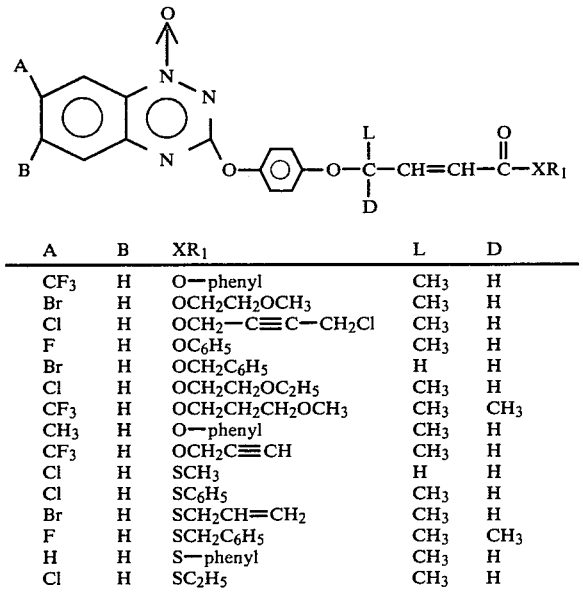

| A | B | XR1 | L | D |
|---|---|---|---|---|
| CF3 | H | O—phenyl | CH3 | H |
| Br | H | OCH2CH2OCH3 | CH3 | H |
| Cl | H | OCH2—C≡C—CH2Cl | CH3 | H |
| F | H | OC6H5 | H | H |
| Br | H | OCH2C6H5 | H | H |
| Cl | H | OCH2CH2OC2H5 | CH3 | H |
| CF3 | H | OCH2CH2CH2OCH3 | CH3 | CH3 |
| CH3 | H | O—phenyl | CH3 | H |
| CF3 | H | OCH2C≡CH | CH3 | H |
| Cl | H | SCH3 | H | H |
| Cl | H | SC6H5 | CH3 | H |
| Br | H | SCH2CH=CH2 | CH3 | H |
| F | H | SCH2C6H5 | CH3 | CH3 |
| H | H | S—phenyl | CH3 | H |
| Cl | H | SC2H5 | CH3 | H |

TABLE IX-continued

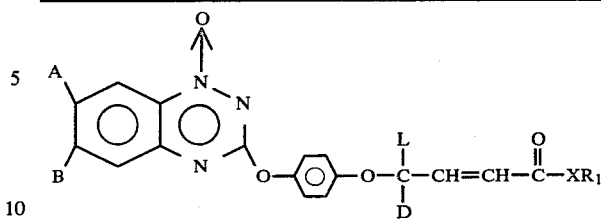

| A | B | XR1 | L | D |
|---|---|---|---|---|
| F | H | SC3H7 | CH3 | CH3 |
| Cl | H | SC4H9 | CH3 | H |
| Cl | H | O—N=C(CH3)2 | CH3 | CH3 |
| Cl | H | O—N=cyclopentylidene | CH3 | H |
| F | H | O—N=CH(C4H9) | H | H |
| Cl | H | O—N=C(CH3)(C2H5) | CH3 | H |
| OMe | H | OCH3 | CH3 | H |

EXAMPLE 12

Sodium 4-[4-[(7-chloro-1-oxide-1,2,4-benzotriazin-3-yl)oxy]phenoxy]pent-2-enoate The method described under Example 5 may be used to prepare the title compound.

By treatment of the appropriate carboxylic acid with a suitable base, the following salts of Formula IIf may be prepared.

TABLE X

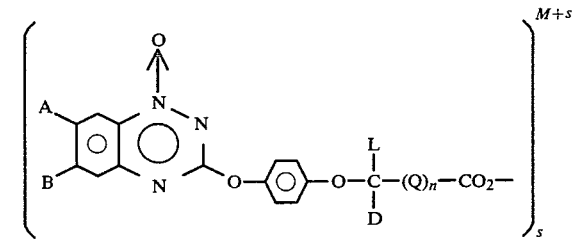

| A | B | S | M | L | D |
|---|---|---|---|---|---|
| H | H | 1 | Na | CH3 | H |
| CF3 | H | 1 | Na | CH3 | CH3 |
| Br | H | 1 | Na | CH3 | H |
| F | H | 1 | Na | CH3 | H |
| F | H | 1 | K | H | H |
| Br | H | 1 | K | CH3 | H |
| Cl | H | 1 | Li | CH3 | H |
| CF3 | H | 1 | Li | CH3 | CH3 |
| CH3 | H | 1 | NH4 | CH3 | H |
| Cl | H | 1 | NH4 | H | H |
| CF3 | H | 1 | CH3NH3 | H | H |
| Cl | H | 1 | (HOCH2CH2)2NH2 | CH3 | H |
| Cl | H | 1 | (CH3)2NH2 | H | H |
| Br | H | 1 | (C2H5)3NH | CH3 | CH3 |
| F | H | 1 | (HOCH2CH2)3NH | CH3 | H |
| Cl | H | 1 | (HOCH2CH2)3NH | CH3 | H |
| Cl | H | 1 | C4H9NH3 | CH3 | H |
| F | H | 2 | Ca | CH3 | H |
| Cl | H | 2 | Ca | CH3 | H |
| Cl | H | 2 | Mg | CH3 | H |
| CF3 | H | 2 | Mg | CH3 | H |
| OCH3 | H | 1 | Na | CH3 | H | where Q = CH=CH.

EXAMPLE 13

Synthesis of methyl 2-(4-hydroxyphenoxy)propanoate

A 42 g (0.25 mole) portion of methyl 2-bromopropionate was added to 0.25 mole of the sodium salt of p-benzyloxyphenol (prepared from 13.5 g sodium methoxide and 50 g p-benzyloxyphenoxy) in 70 cc of DMF. The reaction mixture was heated at approximately 80° C. for 14.5 hours. The cooled reaction mixture was then poured into 1 liter ice-water. The product was isolated by ether extraction and was crystallized from methanol to give 45.2 g methyl 2-(4-benzyloxyphenoxy)propanoate, m.p. 38°–42°.

NMR (CDCl$_3$)δ: 1.6 (d, 3H); 3.7 (s, 3H); 4.6 (q, 1H); 4.9 (s, 2H); 6.8–7 (m, 4H); 7.2–7.6 (m, 5H).

Catalytic hydrogenation at about 45 p.s.i. of 40 g of methyl 2-(4-benzyloxyphenoxy)propanoate in 200 cc of DMF in the presence of 1 g of 10% Pd/c gives methyl 2-(4-hydroxyphenoxy)propanoate in almost quantitative yield. The material is of sufficient purity to be used in the preparation of the compounds of this invention.

NMR (CDCl$_3$)δ: 1.6 (d, 3H); 3.7 (s, 3H); 4.6 (q, 1H); 6.7–6.9 (m, 4H); 8 (s, 1H).

By using a halomalonic acid derivative in lieu of methyl 2-bromopropionate in the procedure of Example 13, other valuable intermediates for preparing compounds where D=CO$_2$R$_8$ and n=0 can be prepared.

EXAMPLE 14

Dimethyl 2-methyl-2-[4-[(7-chloro-1-oxide-1,2,4-benzotriazin-3-yl)oxy]phenoxy]propanedioate The following procedure can be used to prepare the title compound.

In a nitrogen atmosphere, add a solution of 0.02 mole 3-(4-hydroxyphenoxy)-1,2,4-benzotriazine-1-oxide in 30 cc dimethylformamide to 0.8 g (0.02 mole) 57% sodium hydride. When the evolution of hydrogen ceases, add 4.8 g (0.021 mole) dimethyl 2-bromo-2-methylpropanedioate dropwise. When the addition is complete, heat at approximately 70° C. until the reaction is complete. Pour the mixture into ice-water and extract with ether. Concentration of the dry ethereal extracts yields the title compound.

EXAMPLE 15

Methyl 2-(diethylaminocarbonyl)-2-[4-[(7-chloro-1-oxide-1,2,4-benzotriazin-3-yl)oxy]phenoxy]propanoate The procedure outlined below can be used to prepare the title compound.

Add 0.02 mole methyl 2-[(dimethylamino)carbonyl]-2-(4-hydroxyphenoxy)propanoate to 0.02 mole of anhydrous potassium carbonate and 0.02 mole of 3,7-dichloro-1,2,4-benzotriazine-1-oxide in 75 cc of methylethylketone. The reaction mixture is stirred and heated at 80° C. until the reaction is complete. Pour the reaction mixture into water and extract with ether. Concentration of the ethereal extracts gives the desired compound.

Following the teaching of this example and the preceding one, the compounds of Formula IV listed in Table XI can be synthesized.

TABLE XI

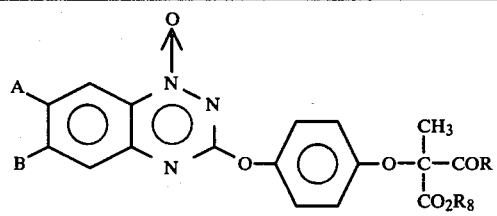

| A | B | R$_8$ | R |
|---|---|---|---|
| Cl | H | CH$_3$— | —OCH$_3$ |
| F | H | C$_2$H$_5$— | —OC$_2$H$_5$ |
| Cl | H | C$_3$H$_7$— | —OC$_3$H$_7$ |
| Cl | H | n-C$_4$H$_9$ | —N(C$_2$H$_5$)$_2$ |
| Br | H | CH$_3$ | —OCH$_3$ |
| F | H | CH$_3$ | —OCH$_3$ |
| Cl | H | C$_2$H$_5$ | —NHC$_4$H$_9$ |
| F | H | C$_2$H$_5$ | —OC$_2$H$_5$ |
| CF$_3$ | H | CH$_3$ | —OC$_2$H$_5$ |
| Br | H | C$_2$H$_5$ | —NHOCH$_3$ |
| OCH$_3$ | H | CH$_3$— | —OCH$_3$ |
| CH$_3$ | H | CH$_3$ | —NH$_2$ |

EXAMPLE 16

Methyl 2-methyl-2-[4-[(7-chloro-1-oxide-1,2,4-benzotriazin-3-yl)oxy]phenoxy]propandioate The procedure described under Example 2 can be used to prepare the desired acid. By hydrolysis of the appropriate diester, the compounds of Formula IV listed in Table XII can be prepared.

TABLE XII

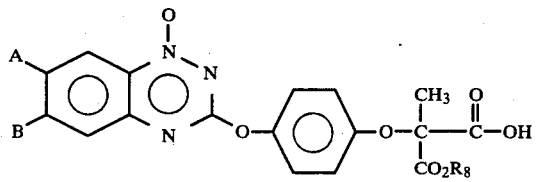

| A | B | R$_8$ |
|---|---|---|
| Cl | H | CH$_3$— |
| H | H | CH$_3$— |
| F | H | C$_2$H$_5$— |
| CF$_3$ | H | C$_2$H$_5$ |
| Cl | H | C$_2$H$_5$ |
| Br | H | C$_2$H$_5$ |
| F | H | CH$_3$ |
| CH$_3$ | H | CH$_3$ |
| OMe | H | CH$_3$ |

EXAMPLE 17

Sodium salt of methyl 2-methyl-2-[4-[(7-chloro-1-oxide-1,2,4-benzotriazin-3-yl)oxy]phenoxy]propanedioate The procedure described in Example 5 can be utilized to prepare the sodium salts.

By careful treatment of the appropriate acid with an equimolar amount of a base, the following salts of Formula IIf may be prepared.

TABLE XIII

[Structure: benzotriazine-1-oxide with A, B substituents on benzene ring, connected via O-phenyl-O-C(CH3)(CO2R8)-CO2⁻ · M^(+s), shown as salt with s subscript]

| A | B | R8 | S | M |
|---|---|---|---|---|
| Cl | H | CH3— | 1 | Na |
| OMe | H | CH3— | 1 | Na |
| CH3 | H | CH3— | 1 | K |
| H | H | CH3— | 1 | K |
| F | H | C2H5— | 1 | Li |
| CF3 | H | C2H5 | 1 | NH4 |
| Cl | H | C2H5 | 1 | (HOCH2CH)2NH2 |
| Br | H | C2H5 | 1 | (C2H5)3NH |
| F | H | CH3 | 1 | t-C4H9NH3 |
| Cl | H | CH3 | 2 | Ca |
| Cl | H | CH3 | 2 | Mg |

EXAMPLE 18

Methyl 2-methyl-3-(methylthio)-3-oxo-2[4-[(7-chloro-1-oxide-1,2,4-benzotriazin-3-yl)oxy]phenoxy]propanoate The acid chloride can be prepared by the addition of the dry sodium salt of the acid (0.1 mole) in small portions to oxalyl chloride (0.12 mole in 200 cc of ether). After 4–5 hours at room temperature, the sodium chloride is removed by filtration and the ether and excess oxalyl chloride are removed under vacuum. The crude acid chloride can be used without any further purification.

The method cited under Example 4 can be utilized to prepare the subject compound.

In an analogous manner, the compounds of Formula IV listed in the following table can be prepared from the acid chloride, appropriate alcohol, thiol, phenol, thiophenol or oxime.

TABLE XIV

[Structure: benzotriazine-1-oxide with A, B on benzene; linked via O-phenyl-O-C(CH3)(CO2R8)-C(=O)-XR1]

| A | B | XR1 | R8 |
|---|---|---|---|
| Cl | H | SCH3 | C2H5 |
| Cl | H | OCH2C6H5 | CH3 |
| F | H | S—n-C4H9 | C3H7 |
| Br | H | SCH2CH=CH2 | CH3 |
| Cl | H | SC6H5 | C2H5 |
| CF3 | H | OC6H5 | CH3 |
| Br | H | OCH2C≡C—CH2—Cl | CH3 |
| Cl | H | OCH3C≡CH | C4H9 |
| CH3 | H | S—n-C4H9 | CH3 |
| Ome | H | SCH3 | CH3 |
| Cl | H | O—N=⬠ (cyclopentylidene) | CH3 |

TABLE XIV-continued

| A | B | XR1 | R8 |
|---|---|---|---|
| Cl | H | O—N=C(CH3)(C2H5) | CH3 |

EXAMPLE 19

Synthesis of methyl 4-(4-hydroxyphenoxy)pentanoate

A 37 g (0.19 mole) sample of methyl 4-bromo-2-pentenoate was added to a mixture of 30 g (0.15 mole) of p-benzyloxyphenol and 25 g (0.18 mole) of potassium carbonate in 200 cc of methylethylketone. The reaction mixture was stirred and refluxed for approximately 18 hours.

The cooled reaction mixture was poured into 400 cc of ice-water and the aqueous solution was extracted once with ether (350 cc). The organic solution was washed with water, saturated sodium bicarbonate, brine and dried over magnesium sulfate. Concentration of the solution gave 36 g of methyl 4-(4-benzyloxyphenoxy)-pentenoate, m.p. 80°–89°.

Catalytic hydrogenation of methyl 4-(4-benzyloxyphenoxy)pentenoate in ethanol over 10% Pd/c gave the title compound as a yellow oil which was purified by silica gel chromatography.

NMR (CDCl3)δ: 1.25 (d, 3H, J=6 Hz); 1.7–2.7 (m, 4H); 3.65 (s, 3H); 3.9–4.4 (m, 1H); 6.5 (s, 1H); 6.78 (s, 4H).

EXAMPLE 20

Methyl 4-[4-[(7-chloro-1-oxide-1,2,4-benzotriazin-3-yl)oxy]-phenoxy]pentanoate

A 0.115 mole sample of 3,7-dichloro-1,2,4-benzotriazin-1-oxide is added to a mixture of 15 g (0.019 mole) of potassium carbonate and 25 g (0.113 mole) of methyl 4-(4-hydroxyphenoxy)pentanoate in 450 cc of acetonitrile. The mixture is refluxed until the reaction is complete and then poured into 300 cc ice-water. The product is isolated by extraction with ether.

Following the teaching of Example 20 and by substituting an appropriate 3-chlorobenzotriazine-1-oxide and alkyl 4-(4-hydroxyphenoxy)alkanoate, the compounds of Formula V of Table XV may be prepared.

TABLE XV

[Structure: benzotriazine-1-oxide with A, B on benzene ring; linked via O-phenyl-O-C(L)(D)-CH2CH2-C(=O)-OR1]

| A | B | L | D | R1 |
|---|---|---|---|---|
| CF3 | H | H | H | CH3 |
| F | H | H | H | CH3 |
| F | H | CH3 | CH3 | CH3 |
| Br | H | CH3 | H | CH3 |

TABLE XV-continued

Structure: benzotriazine N-oxide-O-phenyl-O-C(L)(D)-CH₂CH₂-C(=O)-OR₁

| A | B | L | D | R₁ |
|---|---|---|---|---|
| OCH₃ | H | CH₃ | H | CH₃ |
| CH₃ | H | H | H | CH₃ |
| Cl | H | CH₃ | H | n-C₃H₇ |
| CF₃ | H | CH₃ | H | CH₃ |
| OCH₃ | H | CH₃ | CH₃ | CH₃ |
| Cl | H | H | H | CH₃ |
| F | H | CH₃ | H | n-C₄H₉ |
| Cl | H | CH₃ | H | C₂H₅ |
| Cl | H | CH₃ | H | i-C₃H₇ |
| F | H | CH₃ | H | t-C₄H₉ |
| Cl | H | CH₃ | H | CH₃ |
| CF₃ | H | CH₃ | H | CH₃ |
| Cl | H | H | H | CH₃ |
| Cl | H | CH₃ | H | CH₃ |

EXAMPLE 21

4-[4-[(7-chloro-1-oxide-1,2,4-benzotriazin-3-yl)oxy]-phenoxy]pentanoic acid

The procedure described under Example 2 can be used to prepare the desired acid.

By hydrolysis of the appropriate ester, the compounds of Formula V listed in Table XVI can be prepared.

TABLE XVI

Structure: benzotriazine N-oxide-O-phenyl-O-C(L)(D)-CH₂CH₂-C(=O)-OH

| A | B | L | D |
|---|---|---|---|
| CF₃ | H | CH₃ | H |
| Br | H | CH₃ | H |
| F | H | CH₃ | H |
| Cl | H | H | H |
| Cl | H | CH₃ | H |
| OCH₃ | H | CH₃ | H |
| CF₃ | H | CH₃ | H |
| CH₃ | H | CH₃ | H |
| Cl | H | CH₃ | CH₃ |
| CF₃ | H | CH₃ | H |
| Cl | H | H | H |
| F | H | CH₃ | H |
| Cl | H | H | H |
| Cl | H | CH₃ | H |
| Cl | H | CH₃ | CH₃ |
| Cl | H | CH₃ | H |

EXAMPLE 22

N,N-diethyl-4-[4-[(7-chloro-1-oxide-1,2,4-benzotriazin-3-yl)oxy]phenoxy]pentanamide The method described under Example 3 can be employed to prepare the subject compound. By treatment of the appropriate acid chloride with an amine, using the procedure of Example 3, the amides of Formula V listed in Table XVII can be prepared.

TABLE XVII

Structure: benzotriazine N-oxide-O-phenyl-O-C(L)(D)-CH₂CH₂-C(=O)-N(R₂)(R₃)

| A | B | R₂ | R₃ | L | D |
|---|---|---|---|---|---|
| CF₃ | H | H | H | CH₃ | H |
| Br | H | H | CH₃ | CH₃ | H |
| F | H | cyclohexyl | H | H | H |
| F | H | C₆H₅ | H | CH₃ | H |
| CF₃ | H | C₆H₅CH₂— | H | CH₃ | H |
| OCH₃ | H | H | (CH₃)₂CH | CH₃ | H |
| CF₃ | H | t-C₄H₉ | H | CH₃ | H |
| CH₃ | H | CH₃ | CH₃ | CH₃ | H |
| Cl | H | n-C₄H₉ | CH₃ | CH₃ | H |
| CF₃ | H | —(CH₂)₂—O—(CH₂)₂— | | H | H |
| Cl | H | —(CH₂)₄— | | CH₃ | CH₃ |
| OCH₃ | H | —(CH₂)₅— | | CH₃ | H |
| H | H | —(CH₂)₆— | | CH₃ | H |
| Cl | H | i-C₄H₉ | H | CH₃ | H |
| Cl | H | CH₃ | CH₃O | CH₃ | H |
| Cl | H | C₂H₅ | H | CH₃ | H |
| CF₃ | H | H | phenyl | CH₃ | H |
| Cl | H | —(CH₂)₂—N(CH₃)—(CH₂)₂— | | CH₃ | H |
| Cl | H | H | CH₂—CH=CH₂ | CH₃ | CH₃ |
| Cl | H | H | CH₂CH₂N(CH₃)₂ | CH₃ | H |
| Cl | H | CH₃ | CH₃ | H | H |

EXAMPLE 23

Allyl-2-[4-[(7-chloro-1-oxide-1,2,4-benzotriazin-3-yl)-oxy]phenoxy]propanoate

The method described under Example 4 can be utilized to prepare the title compound.

The compounds of Formula V listed in Table XVIII can be prepared in a similar fashion from the appropriate hydroxy or thio compound.

TABLE XVIII

Structure: benzotriazine N-oxide-O-phenyl-O-C(L)(D)-CH₂CH₂-C(=O)-XR₁

| A | B | XR₁ | L | D |
|---|---|---|---|---|
| CF₃ | H | OC₆H₅ | CH₃ | H |
| Br | H | OCH₂CH₂OCH₃ | CH₃ | H |
| Cl | H | OCH₂—C≡C—CH₂Cl | CH₃ | H |
| F | H | OC₆H₅ | CH₃ | H |
| Cl | H | OCH₃C₆H₅ | H | H |
| OCH₃ | H | OCH₂CH₂OC₂H₅ | H | H |
| CF₃ | H | OCH₂CH₂CH₂OCH₃ | CH₃ | CH₃ |
| CH₂ | H | OC₆H₅ | CH₃ | H |
| CF₃ | H | OCH₂CH=CH₂ | CH₃ | H |
| Cl | H | SCH₃ | H | H |
| H | H | SC₆H₅ | CH₃ | H |
| Cl | H | SCH₂CH=CH₂ | CH₃ | H |
| F | H | SCH₂C₆H₅ | CH₃ | CH₃ |
| Cl | H | SC₆H₅ | CH₃ | H |
| Cl | H | SC₂H₅ | Ch₃ | H |
| F | H | SC₃H₇ | CH₃ | CH₃ |

TABLE XVIII-continued

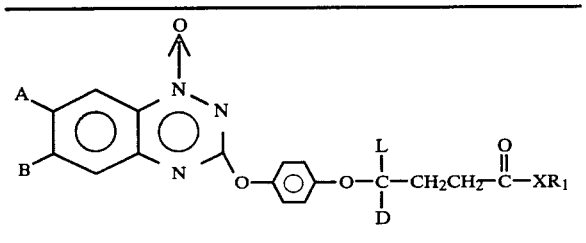

| A | B | XR₁ | L | D |
|---|---|---|---|---|
| Cl | H | SC₄H₉ | CH₃ | H |
| Cl | H | ON=C(CH₃)₂ | CH₃ | CH₃ |
| Cl | H | ON=⬠ | CH₃ | CH₃ |
| F | H | ON=CH(C₄H₉) | CH₃ | H |
| Cl | H | ON=C(CH₃)(C₂H₅) | CH₃ | H |

EXAMPLE 24

Sodium 4-[4-[(7-chloro-1-oxide-1,2,4-benzotriazin-3-yl)oxy]phenoxy]propanoate

The procedure described in Example 5 can be used to prepare the title compound. The compounds of Formula IIf where Q=CH₂CH₂, Y=N, Z=N→O and A, B, S, M, L and D are as defined in Table X can also be prepared in this manner.

EXAMPLE 25

Methyl 2-[4-[(7-chloro-1,4-dioxide-1,2,4-benzotriazin-3-yl)oxy]phenoxy]propanoate This compound can be prepared by oxidation of the compound of Example 1 with excess peracetic acid.

1.5 g of Methyl 2-[4-[(7-chloro-1-oxide-1,2,4-benzotriazin-3-yl)oxy]phenoxy]propanoate is added to 200 ml acetic acid containing 50 ml of 30% H₂O₂ and warmed to 45°–50°. After 40 hours, the mixture is poured into water and the precipitated product is separated.

The compounds of Formula VI in Table XIX are representative of some of the compounds which can be prepared in this manner.

TABLE XIX

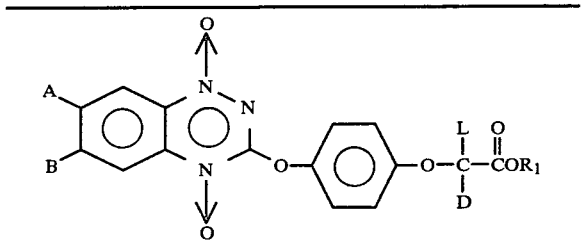

| A | B | R₁ | L | D |
|---|---|---|---|---|
| Cl | H | CH₃ | CH₃ | H |
| Cl | Cl | CH₃ | CH₃ | H |
| CH₃ | H | C₂H₅ | CH₃ | H |
| Cl | H | n-C₄H₉ | CH₃ | H |
| Br | H | CH₃ | CH₃ | H |
| F | H | CH₃ | CH₃ | H |
| CF₃ | H | CH₃ | CH₃ | CH₃ |
| Cl | H | i-C₃H₇ | CH₃ | H |
| Cl | H | t-C₄H₉ | CH₃ | H |
| Cl | H | n-C₃H₇ | CH₃ | H |
| OMe | H | CH₃ | CH₃ | H |

TABLE XIX-continued

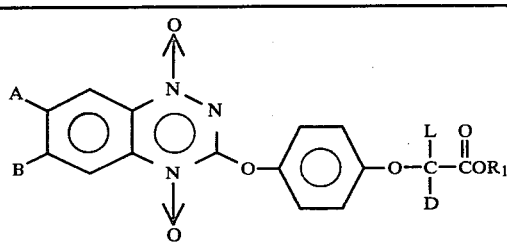

| A | B | R₁ | L | D |
|---|---|---|---|---|
| Cl | H | CH₃ | H | H |

EXAMPLE 26

Methyl 2-[4-[(7-chloro-1,2,4-benzotriazin-3-yl)oxy]phenoxy]propanoate

This compound can be prepared by catalytic hydrogenation of the compound of Example 1 or by reduction of the same compound with zinc in acetic acid. 1.0 g of Methyl 2-[4-[(7-chloro-1-oxide-1,2,4-benzotriazin-3-yl)oxy]phenoxy]propanoate is added to 8 ml of methanol containing 100 mg of Raney nickel catalyst. The mixture is shaken under 1-3 atoms of hydrogen until one mole of hydrogen is absorbed. The catalyst is removed by filtration and the filtrate concentrated to give the product.

The compounds of Formula VII in Table XX are representative of the compounds of this invention.

TABLE XX

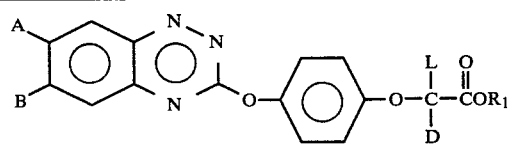

| A | B | R₁ | L | D |
|---|---|---|---|---|
| Cl | H | CH₃ | CH₃ | H |
| Cl | Cl | CH₃ | CH₃ | H |
| CH₃ | H | C₂H₅ | CH₃ | H |
| Cl | H | n-C₄H₉ | CH₃ | H |
| Br | H | CH₃ | CH₃ | H |
| F | H | CH₃ | CH₃ | H |
| CF₃ | H | CH₃ | CH₃ | CH₃ |
| Cl | H | i-C₃H₇ | CH₃ | H |
| Cl | H | t-C₄H₉ | CH₃ | H |
| Cl | H | n-C₃H₇ | CH₃ | H |
| OMe | H | CH₃ | CH₃ | H |
| Cl | H | CH₃ | H | H |

EXAMPLE 27

Methyl 2-[4-[(7-chloro-4-oxide-1,2,4-benzotriazin-3-yl)oxy]phenoxy]propanoate

This compound can be prepared by oxidation of the compound of Example 25 with an equivalent amount of peracetic acid. 0.01 mole Methyl 2-[4-[(7-chloro-1,2,4-benzotriazin-3-yl)oxy]phenoxy]propanoate is added to 100 ml of acetic acid containing 0.01 mole of H₂O₂ (as 30% solution). The mixture is heated at 40°–50° C. until the reaction is complete. The mixture is poured into water and the precipitated product separated.

The compounds of Formula VIII in the following table are representative of the compounds of this invention.

TABLE XXI

A-benzene ring fused with N=N-N(→O) triazine, connected via O to phenyl-O-C(L)(D)-C(=O)-OR₁

| A | B | R₁ | L | D |
|---|---|---|---|---|
| Cl | H | CH₃ | CH₃ | H |
| Cl | Cl | CH₃ | CH₃ | H |
| CH₃ | H | C₂H₅ | CH₃ | H |
| Cl | H | n-C₄H₉ | CH₃ | H |
| Br | H | CH₃ | CH₃ | H |
| F | H | CH₃ | CH₃ | H |
| CF₃ | H | CH₃ | CH₃ | CH₃ |
| Cl | H | i-C₃H₇ | CH₃ | H |
| Cl | H | t-C₄H₉ | CH₃ | H |
| Cl | H | n-C₃H₇ | CH₃ | H |
| OMe | H | CH₃ | CH₃ | H |
| Cl | H | CH₃ | H | H |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XXII

| | Weight Percent* | | |
|---|---|---|---|
| | Active Ingredient | Diluent(s) | Surfactant(s) |
| Wettable Powders | 20–50 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–50 | 5–99.9 | 0–15 |

*Active ingredient plus at least one of a Surfactant or a Diluent equals 100 weight percent.

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 28

| Wettable Powder | |
|---|---|
| Methyl 2-[4-[(7-chloro-1-oxide-1,2,4-benzotrazin-3-yl)oxy]phenoxy]-propanoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 29

| Granule | |
|---|---|
| Wettable Powder of Example 28 | 5% |
| attapulgite granules (U.S.S. 20–40 mesh; 0.84–0.42 mm) | 95% |

A slurry of wettable powder containing solids is sprayed on the surface of attapulgite granules in a double-cone blender. The granules are dried and packaged.

EXAMPLE 30

| Extruded Pellet | |
|---|---|
| Methyl 2-[4-[(7-chloro-1-oxide-1,2,4-benzotriazin-3-yl)oxy]phenoxy]-propanoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 31

| Oil Suspension | |
|---|---|
| Methyl 2-[4-[(7-chloro-1-oxide-1,2,4-benzotriazin-3-yl)oxy]phenoxy]-propanoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 32

| Wettable Powder | |
|---|---|
| Methyl 2-[4-[(7-chloro-1-oxide-1,2,4-benzotriazin-3-yl)oxy]phenoxy]-propanoate | 20% |
| sodium alkylnaphthalenesulfonate | 4% |
| sodium lignisulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 33

| Low Strength Granule | |
|---|---|
| Methyl 2-[4-[(7-chloro-1-oxide-1,2,4-benzotriazin-3-yl)oxy]phenoxy]-propanoate | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 34

| Aqueous Suspension | |
|---|---|
| Methyl 2-[4-[(7-chloro-1-oxide-1,2,4-benzotriazin-3-yl)oxy]phenoxy]-propanoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 35

| Low Strength Granule | |
|---|---|
| Methyl 2-[4-[(7-chloro-1-oxide-1,2,4-benzotriazin-3-yl)oxy]phenoxy]-propanoate | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 36

| Granule | |
|---|---|
| Methyl 2-[4-[(7-chloro-1-oxide-1,2,4-benzotriazin-3-yl)oxy]phenoxy]-propanoate | 50% |
| wetting agent | 1% |
| crude ligninsulfonate salt (containing 5–20% of the natural sugars) | 10% |
| sugars | 39% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 37

| Wettable Powder | |
|---|---|
| Methyl 2-[4-[(7-chloro-1-oxide-1,2,4-benzotriazin-3-yl)oxy]phenoxy]-propanoate | 40% |
| sodium ligninsulfonate | 20% |

-continued

| Wettable Powder | |
| --- | --- |
| montmorillonite clay | 40% |

The ingredients are thoroughly blended, coarsely hammer-milled and then air-milled to produce particles essentially all below 10 microns in size. The material is reblended and then packaged.

EXAMPLE 38

| Dust | |
| --- | --- |
| Methyl 2-[4-[(7-chloro-1-oxide-1,2,4-benzotriazin-3-yl)oxy]phenoxy]-propanoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 39

| Emulsifiable Concentrate | |
| --- | --- |
| Methyl 2-[4-[(7-chloro-1-oxide-1,2,4-benzotriazin-3-yl)oxy]phenoxy]-propanoate | 20% |
| chlorobenzene | 74% |
| sorbitan monostearate and polyoxyethylene condensates thereof | 6% |

The ingredients are combined and stirred to produce a solution which can be emulsified in water for application.

USE

The compounds of the present invention are useful when applied as pre- and/or post-emergence treatments for broad-spectrum control of a wide variety of weed species growing on industrial sites, storage lots, along fences and building foundations, along railroad and utility rights-of-way, etc. In addition, the compounds of the invention have utility for weed control in certain crops, such as soybeans, sugarbeets, sunflowers and beans.

These herbicides are particularly useful for selectively removing and controlling grass weeds, including volunteer corn, in broadleaf crops including soybeans, sugarbeets, beans, flax, cabbage, tomatoes, potatoes, peanuts, carrots, cucurbits, endive, beets, etc. Grass-weeds include, among others, crabgrass, barnyardgrass and wild oats. Compounds of this invention generally show an unexpected degree of safety to broadleaf crops and an unusual phytotoxicity to grass weeds whether applied to the soil before weeds and crops emerge, that is, pre-emergence, or whether applied post-emergence, including spraying on the weeds and crops.

The compounds also are useful when applied as pre-emergence or post-emergence treatments, along and in combination with other herbicides or surfactants, for broad-spectrum control of a wide variety of weed species growing on industrial sites, on storage lots and along fences, building foundations, railroad, highway and utility rights-of-way etc.

The precise amount of the compounds of this invention to be used in any particular situation will vary widely according to the end result desired. Factors affecting the optimum rate of application include the plant species to be controlled, soil type, formulation used, prevailing weather conditions, foliage density, length of time for which residual activity is desired, etc. Broadly speaking, the compounds are used at levels at about 0.005 to 20 kilograms per hectare, preferably approximately 0.06 to 5 kilograms per hectare. In general, the higher rates of application from within this range will be selected for adverse conditions or where extended persistence in soil is desired, and the lower rates for weed control in crops.

The herbicides effectively control grass weeds, as demonstrated by the examples, and may also control some broadleaf weeds. To obtain control of a wider spectrum of both broadleaf and grass weeds, combination treatments consisting of compounds of this invention with other herbicides effective on broadleaf weeds may be used to advantage. Combination treatments may be used with the components applied simultaneously as in a tank mix or mixed formulation, or sequentially with either or both components applied preplant incorporated, pre-emergence, post-emergence, post-emergence-directed, broadcast, band or spot treatment or any combination of these methods. The following examples of combination utility are cited:

| Other Herbicide | Use |
| --- | --- |
| bentazon (post-) | Soybeans |
| 2,4-DB (post-) | Peanuts, Soybeans, Alfalfa, Clover |
| Simazin (pre-) | Nursery, Citrus, Peaches, Established Alfalfa |
| pyrazon (pre-, early post-) | Sugarbeets |
| silvex | Fence lines, rights-of-ways |
| dichloroprop (post-) | Brush, Release of Evergreens |
| MCPB (early post-) | peas |
| dicamba (pre-) | flax and rape |
| desmedipham (post-) | Sugarbeets |
| prometryn (pre-) | Celery and Cotton |
| Phenmedipham (post-) | Sugarbeets |
| acifluorofen (Blazer ®) (post-) | Soybeans |
| 2-chloro-N—[(4-methoxy-6-methyl-1,3,5-triazin-2-yl)aminocarbonyl]benzenesulfonamide | flax |
| 1-methylethyl 2[[(4,6-dimethoxy-1,3,5-triazin-2-yl)aminocarbonyl]]aminosulfonyl]]benzoate | flax |
| 1-methylethyl 2[[(4-methoxy-6-methyl-1,3,5-triazin-2-yl)-aminocarbonyl]aminosulfonyl]-benzoate | flax |
| dinoseb (post-) | Soybeans |
| lenacil (pre-) | Sugarbeets |
| bromaxynil (post-) | Wheat and Barley |
| fluometuron (pre-) | Cotton |
| 1-[2(([(4,6-dimethoxypyrimidin-2-yl)aminocarbonyl]aminosulfonyl))benzoyl]pyrrolidine | Soybeans |
| 2-propenyl(2-[[([4,6-dimethoxy-pyrimidin-2-yl)aminocarbonyll-aminosulfonyl]]benzoate | Soybeans |

TEST A

Seeds of crabgrass (*Digitaria spp.*), barnyardgrass (*Echinochloa crusgalli*), wild oats (*Avena fatua*), cassia (*Cassia tora*), morningglory (*Ipomoea spp.*), cocklebur (*Xanthium spp.*), sorghum, corn, soybean, rice, wheat and nutsedge tubers (*Cyperus rotundus*) were planted in a growth medium and treated pre-emergence with the chemicals dissolved in a non-phytotoxic solvent. At the same time, cotton having five leaves (including cotyledonary ones), bush beans with the third trifoliate leaf expanding, crabgrass and barnyardgrass with two leaves, wild oats with one leaf, cassia with three leaves (including cotyledonary ones), morningglory and cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days. All species were compared to controls and visually rated for response to treatment seven and sixteen days after treatment. The ratings are based on a numerical scale extending from 0=no injury, to 10=complete kill. The accompanying descriptive symbols have the following meanings:

G=growth retardation;
C=chlorosis/necrosis;
E=emergence inhibition;
U=unusual pigmentation; and
B=burn.

The ratings for the compound tested by this procedure are shown in Table A for 16 days after treating.

TABLE A

Methyl 2-[4-[(7-chloro-1-oxide-1,2,4-benzotriazin-3-yl)oxy]phenoxy]propanoate

| kg/ha | 2 |
|---|---|
| POST-EMERGENCE | |
| Bushbean | 1C, 3G |
| Cotton | 3B |
| Morningglory | 2B |
| Cocklebur | 5B, 7G |
| Cassia | 5B, 7G |
| Nutsedge | 0 |
| Crabgrass | 10C |
| Barnyardgrass | 10C |
| Wild Oats | 10C |
| Wheat | 9C |
| Corn | 10C |
| Soybean | 2B, 4G |
| Rice | 10C |
| Sorghum | 10C |
| PRE-EMERGENCE | |
| Morningglory | 0 |
| Cocklebur | 0 |
| Cassia | 0 |
| Nutsedge | 4G |
| Crabgrass | 10E |
| Barnyardgrass | 10E |
| Wild Oats | 10E |
| Wheat | 1C, 8G |
| Corn | 6U, 9G |
| Soybean | 0 |
| Rice | 10E |
| Sorghum | 10E |

TEST B

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria spp.*), nutsedge (*Cyperus rotundus*), barnyardgrass (*Echinochloa crusgalli*), giant foxtail (*Setaria faberii*) and wild oats (*Avena fatua*). At the same time, twelve cm paper cups filled with the same soil were planted to hybrid sunflower, cultivated mustard, and sugarbeets. Approximately 2½ weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table B. It can be seen that the compound tested by this procedure may be useful for the post-emergence control of weeds in several of the major crops.

TABLE 8

Methyl 2-[4-[(7-chloro-1-oxide-1,2,4-benzotriazin-3-yl)-oxy]phenoxy]propanoate

| Rate kg/ha | 0.063 | 0.250 | 1.00 |
|---|---|---|---|
| Soybeans | 0 | 0 | 1G |
| Velvetleaf | 0 | 2G | 6G |
| Sesbania | 1G | 1G | 6G |
| Cassia | 0 | 3C | 3G |
| Cotton | 5G | 5G | 6G |
| Morningglory | 0 | 0 | 6G, 4C |
| Alfalfa | 0 | 0 | 0 |
| Jimsonweed | 0 | 0 | 0 |
| Cocklebur | 0 | 0 | 6G |
| Corn | 0 | 10C | 10C |
| Crabgrass | 7G, 4C | 10C | 10C |
| Rice | 4G, 1C | 9G, 9C | 10C |
| Nutsedge | 0 | 0 | 0 |
| Barnyardgrass | 4G | 6G, 4C | 10C |
| Wheat | 1G | 4G | 6G, 3C |
| Giant Foxtail | 6G | 9G, 9C | 10C |
| Wild Oats | 0 | 7G, 2C | 9G, 8C |
| Sorghum | 1G | 0 | 10C |
| Sunflower | 0 | 0 | 5G |
| Mustard | 0 | 0 | 3G |
| Sugarbeets | 0 | 0 | 4G |

What is claimed is:
1. A compound of the formula:

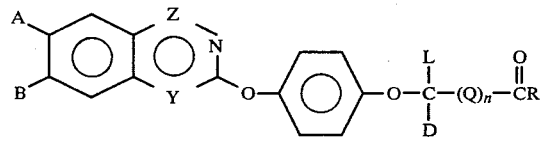

wherein
A is H, Cl, Br, F, $CF_3$, $CH_3$ or $CH_3O$;
B is H or Cl;
D is H, $CH_3$ or $CO_2R_8$;
L is H or $CH_3$;
Q is —CH=CH—;
n is 1;
R is Cl, $XR_1$, $NR_2R_3$, OH or OM;
M is an agriculturally suitable salt;
$R_1$ is $C_1$–$C_4$ alkyl, benzyl, phenyl, $C_5$–$C_8$ cycloalkyl, —$CH_2CH_2OCH_3$, —$CH_2CH_2OCH_2CH_3$, $CH_2CH_2CH_2OCH_3$, $C_3$–$C_4$ alkenyl, $C_3$–$C_4$ alkynyl, —N=$CR_6R_7$ or $C_3$–$C_4$ alkenyl or alkynyl optionally substituted with one Cl;
$R_2$ is H, $C_1$–$C_4$ alkyl, $C_5$–$C_8$ cycloalkyl, benzyl, phenyl, —$OCH_3$, $C_3$–$C_4$ alkenyl or —$CH_2CH_2NR_4R_5$;
$R_3$ is H or $C_1$–$C_4$ alkyl; or
$R_2$ and $R_3$ may be taken together to be —($CH_2$)$_2$—O—($CH_2$)$_2$—, —($CH_2$)$_4$—, —($CH_2$)$_5$—, —($CH_2$)$_6$— or —($CH_2$)$_2$—N—($CH_3$) ($CH_2$)$_2$—;
$R_4$ and $R_5$ are independently methyl or ethyl;
$R_6$ is H or $C_1$–$C_4$ alkyl;

$R_7$ is H or $C_1$-$C_4$ alkyl; or $R_6$ and $R_7$ may be taken together to be $-(CH_2)_5-$ or $-(CH_2)_4-$;

$R_8$ is $C_1$-$C_4$ alkyl;

X is 0 or S; and

Y and Z are independently N or N→O; provided that:

(a) when D is $CO_2R_8$, then n is O and L is $CH_3$;

(b) when $R_1$ is $-N=CR_6R_7$, then X is 0;

(c) $R_2$ and $R_3$ together contain no more than 8 carbon atoms;

(d) one of $R_6$ and $R_7$ is other than H;

(e) when A is other than Cl, then B is H;

(f) when B is Cl, then L is H, D is $CH_3$, n is 0, R is $XR_1$, and X is 0.

2. A compound of claim 1 wherein D is $CH_3$ and L is H.

3. A compound of claim 2 wherein Y is N.

4. A compound of claim 3 wherein $R_1$ is $C_1$-$C_4$ alkyl.

5. A compound of claim 4 wherein n is 0.

6. A composition suitable for controlling the growth of undesired vegetation which comprises an effective amount of a compound of claim 1 and at least one of the following: surfactant, solid or liquid diluent.

7. A composition suitable for controlling the growth of undesired vegetation which comprises an effective amount of a compound of claim 2 and at least one of the following: surfactant, solid or liquid diluent.

8. A composition suitable for controlling the growth of undesired vegetation which comprises an effective amount of a compound of claim 3 and at least one of the following: surfactant, solid or liquid diluent.

9. A composition suitable for controlling the growth of undesired vegetation which comprises an effective amount of a compound of claim 4 and at least one of the following: surfactant, solid or liquid diluent.

10. A composition suitable for controlling the growth of undesired vegetation which comprises an effective amount of a compound of claim 5 and at least one of the following: surfactant, solid or liquid diluent.

11. A method for controlling the growth of undesired vegetation which comprises applying to the locus to be protected an effective amount of a compound of claim 1.

12. A method for controlling the growth of undesired vegetation which comprises applying to the locus to be protected an effective amount of a compound of claim 2.

13. A method for controlling the growth of undesired vegetation which comprises applying to the locus to be protected an effective amount of a compound of claim 3.

14. A method for controlling the growth of undesired vegetation which comprises applying to the locus to be protected an effective amount of a compound of claim 4.

15. A method for controlling the growth of undesired vegetation which comprises applying to the locus to be protected an effective amount of a compound of claim 5.

* * * * *